(12) United States Patent
Kleiner

(10) Patent No.: US 9,398,982 B2
(45) Date of Patent: Jul. 26, 2016

(54) DEVICE FOR USE IN ENDOLUMINAL VACUUM THERAPY

(71) Applicant: Daniel Eduard Kleiner, Roxbury, CT (US)

(72) Inventor: Daniel Eduard Kleiner, Roxbury, CT (US)

(*) Notice: Subject to any disclaimer, the term of this patent is extended or adjusted under 35 U.S.C. 154(b) by 443 days.

(21) Appl. No.: 13/789,784

(22) Filed: Mar. 8, 2013

(65) Prior Publication Data

US 2013/0190706 A1 Jul. 25, 2013

Related U.S. Application Data

(63) Continuation-in-part of application No. PCT/AU2011/001568, filed on Dec. 1, 2011.

(60) Provisional application No. 61/418,549, filed on Dec. 1, 2010, provisional application No. 61/654,898, filed on Jun. 3, 2012.

(30) Foreign Application Priority Data

Feb. 22, 2011 (AU) ................................ 2011900597

(51) Int. Cl.
*A61M 1/00* (2006.01)
*A61F 13/00* (2006.01)
(Continued)

(52) U.S. Cl.
CPC ........ *A61F 13/00068* (2013.01); *A61M 1/0088* (2013.01); *A61F 2013/00536* (2013.01); *A61L 27/56* (2013.01); *A61M 27/00* (2013.01)

(58) Field of Classification Search
CPC ................ A61F 13/00068; A61F 2014/00536; A61M 1/008; A61M 27/00; A61L 27/57
USPC ............................................ 604/319; 29/428
See application file for complete search history.

(56) References Cited

U.S. PATENT DOCUMENTS 3,935,863 A * 2/1976 Kliger ........................... 604/369
4,523,920 A 6/1985 Russo
(Continued)

FOREIGN PATENT DOCUMENTS

CN 101474432 A 7/2009
GB 1534677 A 12/1978
(Continued)

OTHER PUBLICATIONS

Alves et al., "Management of anastomotic leakage after nondiverted large bowel resection," J Am Coll Surg, 1999, 189:554-559.
(Continued)

*Primary Examiner* — Tatyana Zalukaeva
*Assistant Examiner* — Andrew J Mensh
(74) *Attorney, Agent, or Firm* — Maurice M. Klee

(57) ABSTRACT

The device (10, 36, 38, 42, 68) applies a negative pressure to an endoluminal surface in the body of a patient to facilitate healing of a wound in the endoluminal surface. The device comprises a flexible porous element (14) with a peripheral outer face (32) for contact with the wound, the outer face being defined between opposite proximal and distal ends of the porous element. A suction tube (30) for being connected to a suction source externally of the patient's body is provided in fluid communication with the porous element to apply a negative pressure to the wound via the outer face (32) of the porous element (14) upon operation of the suction source. The porous element (14) has at least one through passageway (16) extending from its proximal end to its distal end for passage of bodily substances of the patient through the porous element. The device can also include a drainage tube (22) for collection and drainage of the bodily substances from the patient, wherein the drainage tube is received in the through passageway of the porous element. The device is particularly suitable for assisted healing of anastomotic wounds but its use is not limited thereto.

22 Claims, 9 Drawing Sheets

(51) Int. Cl.
  *A61L 27/56* (2006.01)
  *A61M 27/00* (2006.01)

(56) References Cited

U.S. PATENT DOCUMENTS

| | | | |
|---|---|---|---|
| 4,525,166 A | | 6/1985 | Leclerc |
| 4,533,352 A | * | 8/1985 | Van Beek et al. ............ 604/317 |
| 4,969,880 A | | 11/1990 | Zamierowski |
| 5,045,075 A | | 9/1991 | Ersek |
| 5,100,395 A | | 3/1992 | Rosenberg |
| 5,437,651 A | | 8/1995 | Todd et al. |
| 5,628,735 A | * | 5/1997 | Skow ........................... 604/317 |
| 5,636,643 A | | 6/1997 | Argenta |
| 6,123,697 A | * | 9/2000 | Shippert .......... A61B 17/12022 604/104 |
| 6,235,009 B1 | | 5/2001 | Skow |
| 6,695,823 B1 | | 2/2004 | Lina et al. |
| 7,070,584 B2 | | 7/2006 | Johnson et al. |
| 7,125,402 B1 | | 10/2006 | Yarger |
| 7,128,735 B2 | | 10/2006 | Weston |
| 7,182,758 B2 | | 2/2007 | McCraw |
| 7,438,705 B2 | | 10/2008 | Karpowicz et al. |
| 2004/0054338 A1 | | 3/2004 | Bybordi et al. |
| 2004/0127862 A1 | | 7/2004 | Bubb et al. |
| 2005/0119617 A1 | | 6/2005 | Stecker et al. |
| 2005/0137539 A1 | | 6/2005 | Biggie et al. |
| 2005/0186260 A1 | | 8/2005 | Narini et al. |
| 2005/0222544 A1 | | 10/2005 | Weston |
| 2005/0273066 A1 | | 12/2005 | Wittmann |
| 2006/0036221 A1 | | 2/2006 | Watson, Jr. |
| 2006/0129137 A1 | | 6/2006 | Lockwood et al. |
| 2007/0167926 A1 | * | 7/2007 | Blott et al. .................... 604/304 |
| 2008/0082059 A1 | | 4/2008 | Fink et al. |
| 2008/0161778 A1 | | 7/2008 | Steward |
| 2008/0294147 A1 | | 11/2008 | Radl et al. |
| 2008/0300578 A1 | | 12/2008 | Freedman |
| 2009/0005762 A1 | | 1/2009 | Nishtala et al. |
| 2009/0131892 A1 | | 5/2009 | Karpowicz et al. |
| 2009/0192499 A1 | | 7/2009 | Weston et al. |
| 2009/0234306 A1 | | 9/2009 | Vitaris |
| 2010/0262126 A1 | | 10/2010 | Hu et al. |
| 2012/0123359 A1 | | 5/2012 | Reed |
| 2013/0023840 A1 | * | 1/2013 | Loske et al. .................. 604/319 |

FOREIGN PATENT DOCUMENTS

| | | |
|---|---|---|
| GB | 2356148 B | 6/2004 |
| RU | 1792711 C | 2/1993 |
| RU | 2145241 C1 | 2/2000 |
| SU | 1034746 A1 | 8/1983 |
| SU | 1109175 A1 | 8/1984 |
| WO | 96 08279 A1 | 3/1996 |
| WO | 96 35401 A1 | 11/1996 |
| WO | 99 01173 A1 | 1/1999 |
| WO | 00 21586 S1 | 4/2000 |
| WO | 00 38755 A2 | 7/2000 |
| WO | 00 42958 A1 | 7/2000 |
| WO | 00 47264 A1 | 8/2000 |
| WO | 00 59418 A1 | 10/2000 |
| WO | 00 59424 A1 | 10/2000 |
| WO | 01 85228 A2 | 11/2001 |
| WO | 01 85248 A1 | 11/2001 |
| WO | 02 43634 A2 | 6/2002 |
| WO | 03 018098 A2 | 3/2003 |
| WO | 03 028786 A2 | 4/2003 |
| WO | 03 057070 A2 | 7/2003 |
| WO | 03 057307 A1 | 7/2003 |
| WO | 03 073970 A1 | 9/2003 |
| WO | 2004 018020 A1 | 3/2004 |
| WO | 2004 039424 A1 | 5/2004 |
| WO | 2004 041346 A1 | 5/2004 |
| WO | 2005 082435 A1 | 9/2005 |
| WO | 2006 048240 A1 | 5/2006 |
| WO | 2006 048246 A1 | 5/2006 |
| WO | 2006 056294 A1 | 6/2006 |
| WO | 2006 100053 A2 | 9/2006 |
| WO | 2006 105892 A1 | 10/2006 |
| WO | 2007 015964 A1 | 2/2007 |
| WO | 2007 016664 A1 | 2/2007 |
| WO | 2007 025729 A2 | 3/2007 |
| WO | 2007 030598 A2 | 3/2007 |
| WO | 2007 030599 A2 | 3/2007 |
| WO | 2007 030601 A2 | 3/2007 |
| WO | 2007 031999 A2 | 3/2007 |
| WO | 2007 142688 A1 | 12/2007 |
| WO | 2008 043067 A2 | 4/2008 |
| WO | 2009 114624 A2 | 9/2009 |
| WO | 2009 114786 A2 | 9/2009 |
| WO | 2009 114790 A2 | 9/2009 |
| WO | 2009 117635 A1 | 9/2009 |
| WO | 2009 124100 A1 | 10/2009 |
| WO | 2009 126102 A1 | 10/2009 |
| WO | 2009 126103 A1 | 10/2009 |
| WO | 2010 063466 A1 | 6/2010 |
| WO | 2012 071626 A1 | 6/2012 |
| WO | 2012 123414 A1 | 9/2012 |

OTHER PUBLICATIONS

Arezzo et al., Endoluminal vacuum therapy for anastomotic leaks after rectal surgery. Tech Coloproctol, 2010, 14:279-281.
Bebemelman, WA., "Vacuum assisted closure in coloproctology," Tech Coloproctol, 2009, 13:261-263.MELMAN, WA., "Vacuum assisted closure in coloproctology," Tech Coloproctol, 2009, 13:261-263.
Choi et al., "Leakage after resection and intraperitoneal anastomosis for colorectal malignancy: analysis of risk factors," Dis Colon Rectum, 2006, 49:1719-1725.
Docherty et al., "Comparison of Manually Constructed and Stapled Anastomoses in Colorectal Surgery," Ann Surg, 1995, 221:176-184.
Durai et al., "Perirectal abscess following procedure for prolapsed haemorrhoids," Tech Coloproctol, 2009, 13:307-309.
Gastinger et al. Protective defunctioning stoma in low anterior resection for rectal carcinoma. Br J Surg 2005;92:1137-1142.
Hedrick et al., "Anastomotic leak and the loop ileostomy: friend or foe?," Dis Colon Rectum, 2006, 49:1167-1176.
Matthiessen et al.,"Risk factors for anastomotic leakage after anterior resection of the rectum," Colorectal Dis, 2004, 6:462-469.
Mees et al., "Endo-vacuum assisted closure treatment for rectal anastomotic insufficiency," Dis Colon Rectum, 2008, 51:404-410.
Mekras et al., "Changes in treatment of rectal cancer: increased use of low anterior resection," Tech Coloproctol, 2011, 15 Suppl 1:S51-4.
Morykwas et al., "Vacuum-assisted closure: a new method for wound control and treatment: animal studies and basic foundation," Ann Plast Surg, 1997, 38:553-562.
Norbury et al., "Vacuum-assisted closure therapy attenuates the inflammatory response in a porcine acute wound healing model," Wounds, 2007, 19(4):97-106.
Park et al., "Stoma complications: the Cook County Hospital experience," Dis Colon Rectum, 1999, 42:1575-1580.
Platell et al., "The incidence of anastomotic leaks in patients undergoing colorectal surgery," Colorectal Dis, 2007, 9:71-79.
Ragg et al., "Preoperative risk stratification for mortality and major morbidity in major colorectal surgery," Dis Colon Rectum, 2009, 52:1296-1303.
Urschel et al., "The effect of mechanical stress on soft and hard tissue repair; a review.," Br J Plast Surg, 1988, 41:182-186.
Van Koperen et al., "Endo-sponge treatment of anastomotic leakage after ileo-anal pouch anastomosis: report of two cases," Colorectal Dis, 2008, 10:943-944.
Walker et al., "Anastomotic leakage is predictive of diminished survival after potentially curative resection for colorectal cancer," Ann Surg, 2004, 240:255-259.
Weidenhagen et al., "Endoscopic vacuum-assisted closure of anastomotic leakage following anterior resection of the rectum: a new method," Surg Endosc, 2008, 22:1818-182.
Kleiner, Daniel Eduard, Australian Provisional Application No. 2011900597 entitled "Device for Use in Wound Healing," Australian Patent Office International-Type Search Report (3 pages).
Kleiner, Daniel Eduard, International Application No. PCT/AU2011/001568 entitled "Device for Use in Endoluminal Vacuum Therapy," International Search Report and Written Opinion (13 pages).

* cited by examiner

DEVICE FOR USE IN ENDOLUMINAL VACUUM THERAPY

CROSS REFERENCE TO RELATED APPLICATIONS

This application is a continuation-in-part under 35 USC §120 of International Application No. PCT/AU2011/001568 filed Dec. 1, 2011 which designated the United States and which claims the benefit under 35 USC §119(e) of U.S. Provisional Application No. 61/418,549 filed Dec. 1, 2010 and claims the benefit under 35 USC §119(a) of Australian Provisional Application No. 2011900597 filed Feb. 22, 2011. This application also claims the benefit under 35 USC §119(e) of U.S. Provisional Application No. 61/654,898 filed Jun. 3, 2012. The contents of International Application No. PCT/AU2011/001568, U.S. Provisional Application No. 61/418,549, Australian Provisional Application No. 2011900597, and U.S. Provisional Application No. 61/654,898 are hereby incorporated by reference in their entireties.

FIELD OF THE INVENTION

The invention relates to a device for facilitating healing of a wound in an endoluminal surface of a patient and a method for use of the device.

BACKGROUND OF THE INVENTION

Cancer remains one of the major modern day health issues and accounts for a large proportion of health and hospital costs. For example, in excess of 106,000 new cases of large bowel cancer are diagnosed each year in the United States alone. Of these, about 65,230 cases are colon cancer while the remainder of patients have cancer of the rectum. In the United States, approximately 49,920 people die from colorectal cancer (CRC) yearly, with about 1 in 17 people developing CRC during some stage of their life.

Surgery is the mainstay of care for CRC. Radiotherapy (for rectal cancer) and/or chemotherapy can also be administered. About 60% of rectal cancer patients have surgery as well as both radiotherapy and chemotherapy. Surgery involves resection of the affected region and rejoining of the bowel forming an anastomosis. Commonly, a colostomy involving attaching the top end of the colon to an opening (known as a stoma) made in the abdomen is performed to divert faecal matter away from the anastomosis to a collection bag arranged externally of the patient's body while the anastomosis is healing. Connection of the lower end of the small intestine (the ileum) to the stoma is known as an ileostomy. The colostomy or ileostomy is usually temporary requiring a subsequent reversal operation to be performed.

A patient who has a rectal cancer, for example, may have a Lower Anterior Resection (LAR). Of such patients in the United States, about 32% will undergo a temporary diverting loop ileostomy. A patient that has an LAR but not an ileostomy has a 10-30% risk of having an anastomotic leak which can be either symptomatic (10-15%) or asymptomatic. However, patients that suffer anastomotic leakage not only then require an ileostomy, an abscess can form at the site of the leakage which then requires drainage, involving a yet further operation complicating the healing process. If the leakage is symptomatic the mortality rate is 6-22%.

The average time to surgical reversal of a colostomy or ileostomy is about 15 to 23 weeks. Immediately prior to the reversal, a contrast (e.g., barium) enema is performed to ensure that the anastomosis has healed. A routine reversal is not without its own risks, with the overall complication rate (e.g., wound infection etc) estimated at about 19.8%. About 3% of patients suffer an anastomotic leak associated with the reversal operation. Moreover, in the United States, the financial cost for the colostomy or ileostomy and subsequent reversal can be US$10,000 to $15,000 or more per patient.

As such, not only is there significant morbidity and mortality associated with anastomotic leakage arising from primary surgery for treatment of CRC, the risk of leakage is compounded by subsequent diverting colostomy/ileostomy procedures and reversal operations where performed, the latter treatments adding significantly to the financial burden involved in obtaining treatment.

The application of sub-atmospheric pressure to acute or chronic wounds to promote wound healing is known as negative pressure wound therapy (NPWT) or vacuum assisted closure (VAC). VAC therapy involves creating a negative-pressure in the local wound environment, drawing away bacteria, exudate, fluid and desiccated tissue from the wound site. Besides improving localised conditions and reducing oedema for wound healing, the negative pressure may draw wound edges together and increase the rate of healing by promoting blood flow and facilitating localised cell migration and proliferation. Indeed, it is believed VAC therapy can increase the rate of wound closure.

Conventionally, VAC therapy has been applied to wounds in the skin such as burns, grafts, surgical incisions, diabetic ulcers, pressure ulcers, venous stasis ulcers and wounds arising from trauma. These "wound VAC" devices comprise a pad of open-cell sponge like material or a porous mat for being placed on the wound. A vacuum is applied to the sponge via a drainage tube through which fluid and exudate from the wound that is drawn into the sponge or mat is drained away. A drape can be laid over the sponge or porous mat to facilitate sealing of the wound. Such devices are commercially available and, for example, are described in U.S. patent application Ser. Nos. 11/186,056, 11/347,073, 11/409,116, 11/268,212, 12/233,211, and International Patent Application WO 93/09727. In more recent times, VAC devices comprising like porous sponges and mats have been used to drain seromas and fluids from internal bodily spaces following surgery and to facilitate the healing of wounds on outer surfaces of internal body organs and tissues, examples of which are described in WO 03/028786, U.S. Pat. No. 5,437,651 and patent application Ser. No. 11/646,918.

SUMMARY OF THE INVENTION

Broadly stated, the present invention relates to the provision and use of a vacuum assisted closure (VAC) type device to facilitate the healing of a wound in an endoluminal surface within the body of a patient. Whilst, in at least some forms, devices embodied by the invention have application in the treatment of anastomotic wounds resulting from surgery such as for colorectal cancer (CRC), the invention is not limited thereto.

In particular, in an aspect of the invention there is provided a device for applying a negative pressure to an endoluminal surface in the body of a patient to facilitate healing of a wound in the endoluminal surface, comprising:

a flexible porous element with a peripheral outer face for contact with the wound, the outer face being defined between opposite proximal and distal ends of the porous element; and a suction tube for being connected to a suction source externally of the patient's body and which is in fluid communication with the porous element to apply a negative pressure to the wound via the outer face of the porous element upon operation of the suction source, the porous element having at least one through passageway extending from its proximal end to its distal end for passage of bodily substances of the patient through the porous element, and at least one of the proximal and distal ends of the porous element is otherwise adapted against egress of the bodily substances into the porous element.

Typically, both the proximal and distal ends of the porous body are otherwise adapted against egress of the bodily substances into the porous element.

The porous element can be cylindrical with a single longitudinal said through passage, the through passage being defined substantially centrally within the porous element.

In other embodiments, the porous element is funnel shaped with a projecting shaft for being inserted into a duct defined by the endoluminal surface, the through passageway extending longitudinally through the shaft. Typically, the device further comprises a drainage tube for drainage of the bodily substances that pass through the porous element from the body of the patient.

Typically, the drainage tube is received in the through passageway of the porous element and the interior of that portion of the drainage tube within the porous element is sealed from the surrounding porous element by the side wall of the drainage tube to ensure the suction is applied to the peripheral outer face of the porous element via the suction tube.

In at least some embodiments, the drainage tube projects from the proximal and distal ends of the porous element, wherein the interior of the drainage tube is defined by a peripheral side wall of the tube and a plurality of through openings are provided in the side wall forward of the proximal end of the porous element for entry of the bodily substances into the interior of the drainage tube. In at least some embodiments, a plurality of further through openings may also, or alternatively, be provided in the side wall of the drainage tube rearwardly of the distal end of the porous element.

A device embodied by the invention may also comprise an expandable element arranged for expanding the porous element to press the outer face of the porous element against the wound with expansion of the expandable element. In embodiments provided with a drainage tube, the expandable element can be disposed between the discharge tube and the porous element.

The expandable element can be an inflatable inner core of the porous element. Alternatively, the expandable element can be fabricated from a resilient material biased to an expanded normal resting state or, for example, comprise an expandable stent.

A device in accordance with the invention can also comprise a hollow locating tube for receiving the porous element within the interior of the locating tube to facilitate location of the porous element in position adjacent the endoluminal surface. In such embodiments, the expandable element is in a compressed deflated or collapsed state when the porous element is received within the locating tube, and expands (or is expanded) upon the tube being withdrawn from about the porous element, or the porous element otherwise being ejected from the locating tube, to press the porous element against the wound.

Typically, the porous element is formed from an absorbent material. The absorbent material can, for instance, be a sponge.

In another aspect of the invention there is provided a method for facilitating healing of a wound in an endoluminal surface in a body of a patient, comprising:

providing a device for applying a negative pressure to the wound, the device having a flexible porous element with a peripheral outer face for contact with the wound, the outer face being defined between opposite proximal and distal ends of the porous element, the porous element having at least one through passageway extending from its proximal end to its distal end for passage of bodily substances of the patient through the porous element, and at least one of the proximal and distal ends of the porous element is otherwise adapted against egress of the bodily substances into the porous element;

locating the device in position such that the peripheral outer face of the porous element is in contact with the wound; and applying a negative pressure to the endoluminal surface through the outer face of the porous element via a suction tube in fluid communication with the porous element.

In another aspect of the invention there is provided a method for treating, or reducing potential for, leakage from an anastomosis in an endoluminal surface in a body of a patient, comprising:

providing a device for applying a negative pressure to the anastomosis, the device having a flexible porous element with a peripheral outer face for contact with the anastomosis, the outer face being defined between opposite proximal and distal ends of the porous element, the porous element having at least one through passageway extending from its proximal end to its distal end for passage of bodily substances of the patient through the porous element, and at least one of the proximal and distal ends of the porous element is otherwise adapted against egress of the bodily substances into the porous element;

locating the device in position such that the porous element is in contact with the anastomosis; and applying a negative pressure to the anastomosis through the outer face of the porous element via a suction tube in fluid communication with the porous element.

Besides wounds arising from surgical resection, other wounds that may be treated using a device embodied by the invention include those arising from diseases and physiological conditions, ablation, radiotherapy, chemotherapy or other medical treatments, and injuries due to accidents and trauma. Moreover, although at least some embodiments are particularly suitable for use in facilitating healing of an anastomotic or other wound in the endoluminal surface of the large bowel of the gastrointestinal tract as described above, devices in accordance with the invention may have application in other luminal structures such as those as may be explored with an endoscope or similar type of viewing device.

In particularly preferred embodiments, the device can be mounted on an endoscope and located in position within the lumen with the use of the endoscope (or other suitable insertion or viewing device). A guide wire can also be inserted along the relevant lumen, a device embodied by the invention moved along the guide wire into position, and the guide wire then withdrawn leaving the device behind within the lumen. This can be done under e.g., ultrasound or fluoroscopic guidance. As the porous element of a device embodied by the invention is provided with a through passageway as described above, bodily substances present within the lumen may be diverted through the porous element essentially without reducing the suction applied to the wound as a result of the porous element becoming clogged or fouled by them. Moreover, in instances of surgery on the large bowel, as bodily substances (e.g., faecal matter) can pass through the porous element via the through passageway while the device is in position in use, the need for a diverting colostomy or ileostomy following resection of tissue for treatment of CRC may also be reduced or avoided altogether. By avoiding the need for a colostomy or ileostomy, not only may the significant financial burden associated with patient treatment be lessened, patient psychological stress and discomfort stemming from the need for the patient to wear a waste collection bag into which bodily waste is received via the stoma is also avoided.

In addition, the use of a device as described herein may in one or more embodiments of the invention increase the rate of healing of the wound in the endoluminal surface of the patient. The risk of anastomotic leakage and associated morbidity and mortality may also be reduced in patients following surgery such as an LAR on whom a diverting loop ileostomy is not performed.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like that has been included in this specification is solely for the purpose of providing a context for the invention. It is not to be taken as an admission that any or all of these matters form part of the prior art base or were common general knowledge in the field relevant to the invention as it existed in Australia or elsewhere before the priority date of this application.

The features and advantages of the invention will become further apparent from the following detailed description of embodiments thereof together with the accompanying drawings. At least some like components of different embodiments of devices of the invention are numbered the same for convenience in the following description.

BRIEF DESCRIPTION OF THE ACCOMPANYING DRAWINGS

DETAILED DESCRIPTION OF EXEMPLARY EMBODIMENTS OF THE INVENTION

Figure 1:
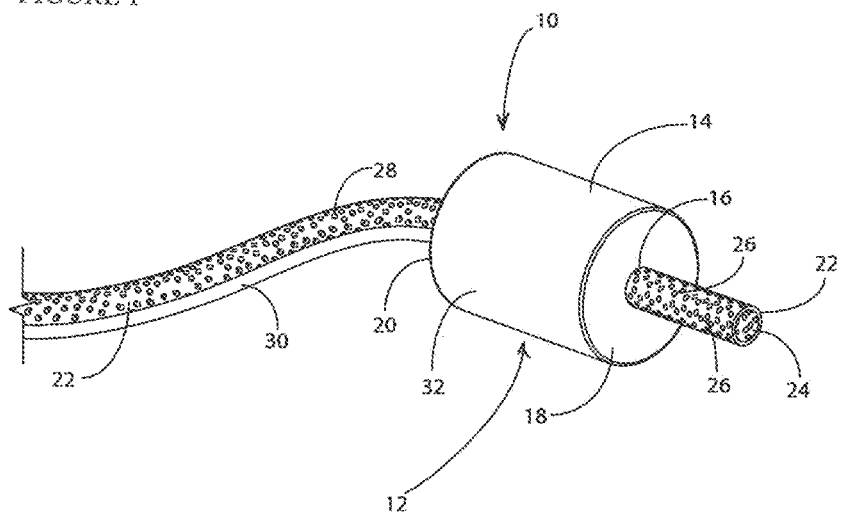
FIG. 1 is a diagrammatic perspective view of a device embodied by the invention.

A device 10 embodied by the invention (termed an endo-Vac herein) is shown in FIG. 1. The device comprises a porous element 12 in the form of a substantially cylindrical biocompatible sponge 14 with a peripheral outer face for contact with an endoluminal surface of a patient and having a central through passageway indicated by the numeral 16 that extends from a proximal end 18 of the sponge to its opposite distal end 20. A drainage tube 22 fabricated from a physiologically acceptable plastic material is received in the through passageway of the sponge. The drainage tube allows for passage of bodily substances through the sponge and drainage from the lumen of the patient in use as further described below.

As can be seen, the drainage tube protrudes from the proximal end of the sponge 14 and terminates in an open end 24 for entry of the bodily substances into the tube. Further openings 26 for entry of the bodily substances into the interior of the drainage tube are provided in the side wall of the tube forward of the sponge. As also indicated in FIG. 1, the drainage tube 22 extends from the distal end 20 of the sponge, and is of a length sufficient to extend from the patient's body. Additional openings 28 are provided in the side wall of the tube for entry of bodily substances into the interior of the tube rearwardly of the sponge. That portion of the drainage tube 22 within the sponge is unperforated thereby sealing the interior of the drainage tube from the surrounding sponge. The sponge is fixed to the drainage tube along its length so as to retain the sponge in position whilst the device 10 is being inserted into position within the lumen. The sponge may be fixed to the tube by, for example, by the use of a suitable adhesive, or sonic or heat welding.

A suction tube 30 for connection to a suction source arranged externally of the patient's body is in fluid communication with the sponge 14 for application of a negative pressure to the sponge. Both the proximal and distal ends 18 and 20 of the sponge are essentially impermeable to gases and fluids, and so are adapted against egress of the bodily substances into the sponge under action of the suction applied to the sponge via the suction tube.

To seal the proximal and distal ends of the sponge against entry of the bodily substances, an occlusive barrier in the form of a ring of flexible plastic sheet material can be affixed to the respective ends in any suitable manner such as by an appropriate adhesive, heat or sonic welding, or other method. In this embodiment, the suction tube is sealingly received in, or terminates about, an opening provided in the ring of plastic sheeting affixed to the distal end of the sponge whereby the interior of the suction tube is in fluid communication with the sponge. Alternatively, the sponge can be provided with a flexible annular end cap formed from a suitable plastics material (e.g., a closed cell foam) that sealingly receives the suction tube and is affixed to the distal end of the sponge for application of the suction to the sponge via the suction tube. In such embodiments, the suction tube can open into a circumferential open channel defined in the underside of the annular cap wherein the open channel faces the distal end of the sponge for more even circumferential distribution of the applied suction to the sponge. Preferably, however, in other forms, the suction tube 30 extends into the sponge itself and has through openings in the side wall of that portion of the suction tube within the sponge. In still further embodiments, an essentially impermeable coating can be applied to the respective end(s) of the sponge to seal the proximal and/or distal end(s) of the sponge rather than employing sheet plastics material or end/caps for this purpose.

Figure 2:
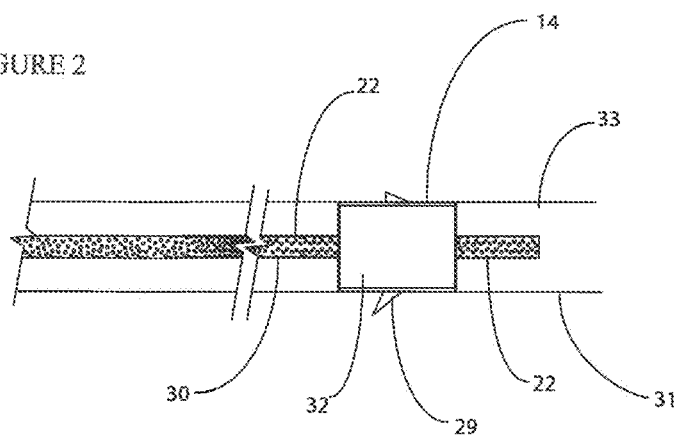
FIG. 2 is a diagrammatic partial side view of a the device of FIG. 1 in position within a lumen in the body of a patient.

The interior of the drainage tube is separated from the sponge along the entire length of the tube within the through passageway by the side wall of the tube. That is, there are no through openings in the side wall of the drainage tube between the proximal and distal ends of the sponge 14 ensuring the suction is applied to the peripheral face However, and with reference to FIG. 2, the peripheral outer face 32 of the sponge is in fluid communication with the suction tube through pores in the sponge, and is pressed against the wound 29 in the surrounding endoluminal surface 31 defining the lumen 33 in which the device 10 is placed in use. When in position, suction from the external suction source is thereby applied to wound and surrounding endoluminal surface via the peripheral outer face of the sponge 14. This creates a localised area of negative pressure about the wound, the suction drawing surface fluid and any exudate that may be present away from the wound into the sponge.

Thus, besides providing suction to the sponge, the suction tube 30 acts as a second drainage tube for fluids drawn through the sponge from the wound. Moreover, by diverting bodily substances present in the lumen through the sponge via the through passageway 16 and thereby separating those substances from fluids drawn into the sponge from the wound, clogging and/or fouling of the sponge by the bodily substance(s) in the lumen and associated loss of suction applied to the wound via the suction tube may be reduced or avoided.

Other endoVAC devices embodied by the invention similar to that shown in FIG. 1 are also provided but which have an expandable element 34 disposed in the through passageway 16 of the sponge and more particularly, between the drainage tube 22 and the outer cylindrical layer of sponge 14. The expandable element is arranged to expand the sponge to press the peripheral outer face 32 of the sponge into firm with contact with the endoluminal surface, and can take various forms.

Figure 3:
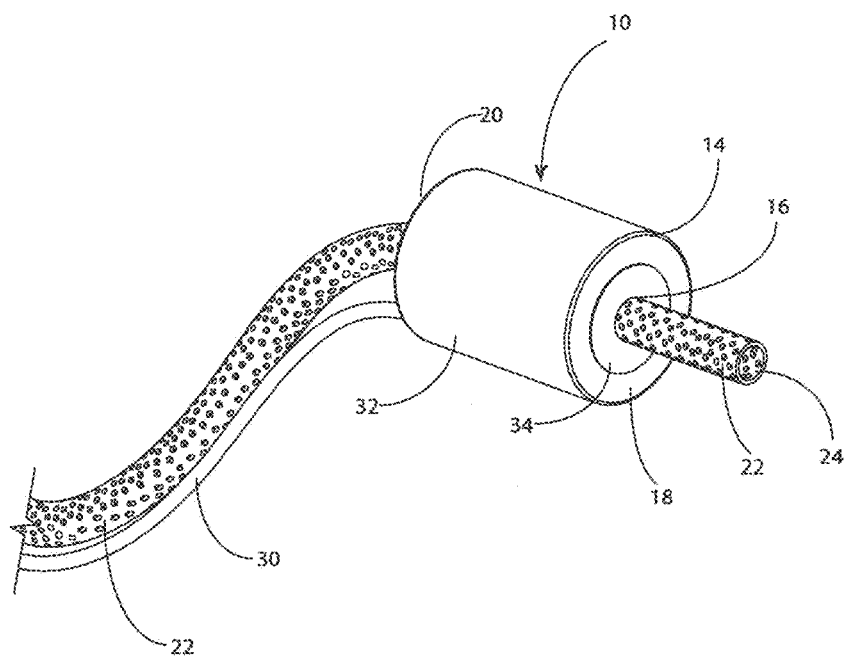
FIG. 3 is a diagrammatic perspective view of another device embodied by the invention.

For instance, in the embodiment illustrated in FIG. 3, the expandable element 34 is in the form of a tubular insert fabricated from a resilient material (e.g., a foamed plastics material) that is maintained in a compressed state about the drainage tube by a hollow locating tube/sheath (not shown) in which the surrounding sponge 14 is received whilst the device 10 is being located in position with the lumen adjacent the wound to be treated. The resilient material is biased to a normally expanded resting condition, and expands to that condition to press the sponge against the wound and surrounding endoluminal surface upon the insertion tube or sheath being withdrawn from the sponge once the device has been positioned within the lumen.

In another form, a further suction tube can be provided for applying suction/negative pressure to the resilient insert to compress the insert without the need to use a locating tube. In this embodiment, the peripheral surface of the resilient insert facing the sponge is sealed from the sponge (e.g., by an impermeable coating). As with the sponge 14, the proximal and distal ends of the insert are also sealed either by, for example, an impermeable coating or barrier as described in relation to FIG. 1. As such, withdrawal of the negative pressure applied to the resilient insert via the further suction tube allows the insert to expand to its normal resting condition and press the peripheral outer face of the sponge against the endoluminal surface.

Figure 4:
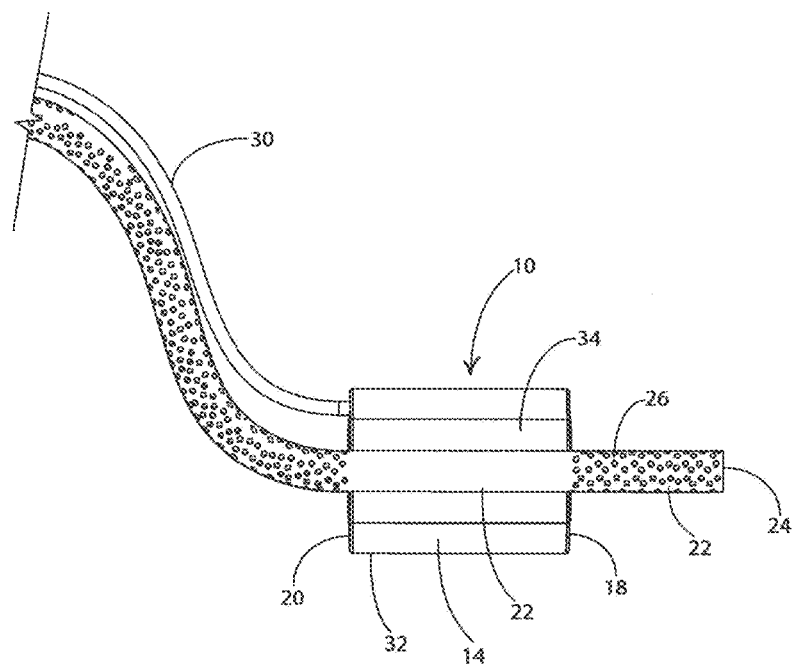
FIG. 4 is a diagrammatic perspective view of another device embodied by the invention.

As a still further alternative, the expandable element 34 can take the form of an inflatable insert such as a tubular balloon with an inflation tube for inflation of the balloon to expand the peripheral outer face of the sponge into pressed contact with the endoluminal surface as generally illustrated in FIG. 4. The inflation tube can, for example, be connected to a hand operated pump externally of the patient's body for effecting inflation of the balloon to a predetermined pressure. To avoid over inflation, the pump is provided with a pressure safety valve and/or in other forms, a pressure gauge for indicating the pressure applied to the balloon. Once suitably inflated, a valve of the pump is closed to retain the balloon in the inflated condition.

From the above it will be understood that the term "expandable element" as used herein encompasses elements that can expanded from a compressed, collapsed or deflated condition in use to press the peripheral outer surface of the sponge 14 against the endoluminal surface. As such, the expandable element may normally exist in an expanded condition. Further, it will be appreciated that collapsing or compressing the sponge (with or without the use of a locating tube or sheath as described above) may assist passage of the device along the relevant bodily lumen into position by minimising frictional contact with the endoluminal surface.

Figure 5:
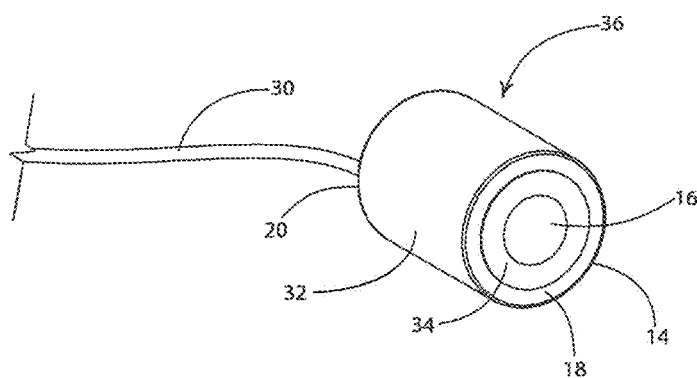
FIG. 5 is a diagrammatic perspective view of yet another device embodied by the invention.

Whilst the provision of a drainage tube 22 is desirable, it is not essential and embodiments of devices of the invention can be provided without one as illustrated in FIG. 5. In this embodiment, bodily substances present within the lumen may simply pass through the through passageway 16 of the device 36 once the device is located in position.

When provided, the drainage tube can be connected to a programmable or other electric suction pump for drawing the relevant bodily substances through the device 10, 36 to assist drainage and sanitary collection of the substances from the patient for monitoring and/or subsequent disposal. The external suction source connected to the suction tube 30 may also be an electric pump although any suitable source of suction can be utilised. In embodiments of a device of the invention that is provided with a suction compressible resilient insert 34 as described above, that insert may be connected to the same or different suction source as the sponge 14. Typically, the suction applied to the sponge 14 via the suction tube 30 will be in a range of from 11 mm Hg to 140 mm Hg and most usually, in a range of from 50-100 mm Hg.

Various types of sponge 14 suitable for use in a device of the invention are known, non-limiting examples of which may include open cell polyurethane and polyvinyl alcohol foams with or without a reticulated cell structure. The pores of the sponge may be in a range of from about 100 μM to about 1000 μM, more usually in a range of from about 200 μM to 600 μM and generally, in a range of from about 400 μM to 600 μM. Desirably, the foam employed is essentially non-adherent to the wound. Alternatively, the device can be removed from the patient before any deleterious adherence to the wound or tissue ingrowth into the sponge 14 occurs. In other embodiments of a device in accordance with the invention, the absorbent material from which the porous element 12 or sponge 14 is formed may be a suitable gauze or wadding conventionally used for the treatment of wounds.

EndoVAC devices embodied by the invention have particular application in the treatment of anastomotic wounds following surgery of the large bowel of the gastrointestinal (GI) tract for removal of cancerous tissue and to provide clear tissue margins in colorectal cancer (CRC) patients. Prior to the surgery (e.g., 24 hours beforehand), the patient's bowel is cleared of stool by the administration of laxatives such as dipropylene glycol and/or anemas. For cancer of the cecum or ascending colon, for example, a right hemicolectomy may be performed, whilst an extended hemicolectomy may be performed for cancer of the transverse colon. In patients with cancer of the descending or sigmoid colon, the surgery typically involves a left hemicolectomy or sigmoidectomy. In each of these surgeries, an anastomotic wound is formed by joining resected tissues and may be treated in accordance with the invention.

To facilitate healing of the wound, the endoVAC device of the invention is inserted into position adjacent the wound in the large bowel via the anus. An endoscope type viewing device such as a rigid or semi-flexible sigmoidoscope or colonoscope with a slight curvature may be employed to locate the device in position. The endoVAC device may be mounted on the end of the endoscope and/or otherwise be moved along the lumen of the large bowel as the endoscope is inserted into the patient. When in position adjacent the wound, the endoscope or other locating tool is withdrawn from the patient, the sponge is expanded into pressed contact with the endoluminal surface of the large bowel as needed as described above, and suction is applied to the sponge 14 via connection of the sponge to the external sectional suction source by the suction tube 30. A guide wire or tendon may also be inserted along the lumen, and a device embodied by the invention then moved along the guide wire into position before the guide wire is removed. To assist positioning, the location of the device can be monitored by ultrasound or, for example, a fluoroscopic technique employing a contrast agent by another surgeon or medical attendant.

The endoVAC device will generally be maintained in position and negative pressure applied to the anastomotic wound for 3 to 5 days while the wound heals. During this time, faecal matter, mucus, and other fluid bodily substances in the large bowel distally to the device can pass through the sponge via the through passageway 16 or drainage tube 22 when provided.

Besides the large bowel, an endoVAC device embodied by the invention may, for example, be utilised to assist healing of fallopian tube, tracheal, bronchial, oesophagus, esophagogastric, gastrojeuneal or pancreatojejunal wounds such as following esophagectomy or bariatric surgery. Indeed, it will be understood that the endoluminal surface can be any endoluminal surface amenable to treatment with a device as described herein. Moreover, besides wounds resulting from resection of tissue, a device as described herein has application to assisted healing of wounds resulting from, but not limited to, trauma, radiotherapy, radiofrequency ablation, ethanol ablation, cryosurgery, chemotherapy, polypectomies, and ulcers. Hence, the term "wound" as used herein is to be taken in its broadest context to encompass wounds inflicted by surgery and medical treatments, trauma caused by accidents, and wounds resulting from physiological diseases or conditions (e.g., a fistula). Further, the term "bodily substances" as used herein is to be taken to encompass air, gases, fluids, mucous and waste bodily products (e.g., faecal matter) that may be present within the relevant lumen of the patient.

Employing a device in accordance with the invention may, in one or more embodiments, allow for a colostomy or ileostomy associated with surgery of the large bowel such as for CRC (e.g., Lower Anterior Resection (LAR)), and the risk of anastomotic leakage connected with subsequent reversal of the colostomy or ileostomy, to be avoided. Likewise, by facilitating the healing of anastomotic wound, the risk of leakage and/or infection of the wound may be decreased. To further facilitate healing, in at least some embodiments, the sponge or other porous element 12 may be impregnated or coated with drugs or other therapeutic agents such as antibiotics for release at, or application to, the wound site. For instance, a silver ion releasing antimicrobial coating may be applied to the peripheral outer face of the sponge for application to the wound. Moreover, by providing an occlusive barrier to the proximal and/or distal ends of the sponge 14 against the egress of gases, faecal matter and/or bodily fluids into the sponge 14 as described above, bacterial loading and "clogging" of the sponge 14 may be minimised.

Figure 6:
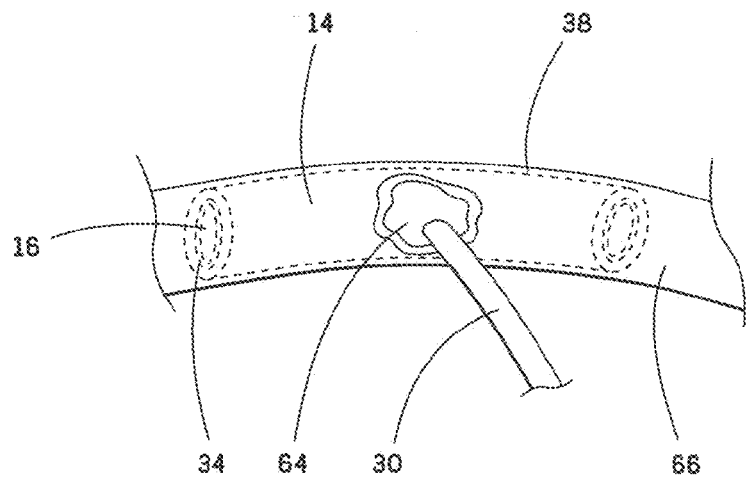
FIG. 6 is a diagrammatic view of a further device embodied by the invention in position within a lumen in the body of a patient.

An endoVAC device embodied by the invention may also be used to assist the healing of a fistula between e.g., the bowel and skin as generally illustrated in FIG. 6. In this embodiment, the device 38 is of the type having an expandable element 34 to press the surrounding sponge 14 into contact with the endoluminal surface of the bowel lumen 66 into which the fistula 64 opens. However, rather than the suction tube 30 applying suction to the distal end of the sponge or otherwise entering the distal end of the sponge, in this instance, the suction tube enters the device 38 through the side of the sponge and protrudes from the subject's body through the fistula. The suction tube can, for example, fork within the sponge such that one fork of the suction tube extends distally along within the sponge from the middle of the sponge and the other fork extends along within the sponge in the opposite direction to distribute the applied suction along the length of the sponge. The endoVAC device 38 can be inserted into position in the bowel through the fistula, and suction applied to the endoluminal surface around the fistula to promote healing. As healing of the fistula progresses and the tissue forming the opening of the fistula into the bowel is remodelled, the device 38 can be replaced with another device 38 of a smaller size by removing the previous device through the fistula and reinserting the smaller device in the same manner. Depending on the size of the fistula, this may be repeated one or more times.

Figure 7:
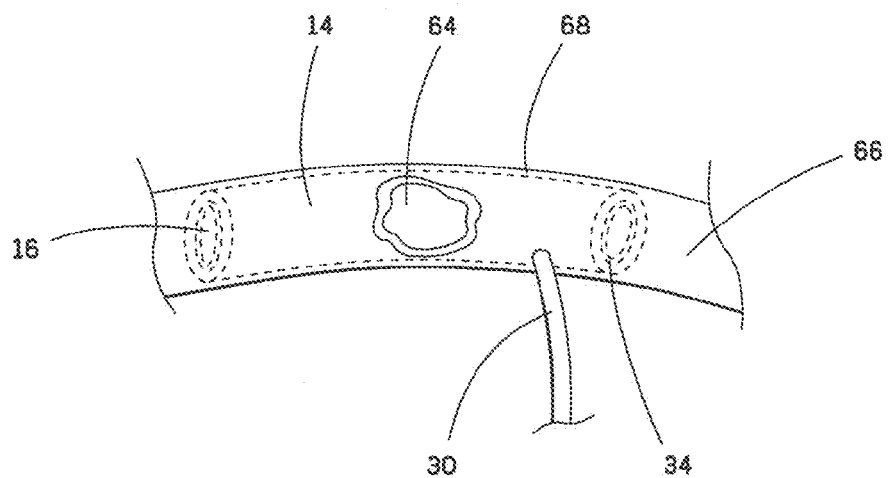
FIG. 7 is a diagrammatic view of a further device embodied by the invention in position within the lumen in a body of a patient.

In another embodiment, an endoVAC device 68 can be located in position within the bowel so as to cover the opening of a fistula 64 but wherein the suction tube 30 enters the bowel through a surgically made opening along from the fistula as illustrated in FIG. 7.

Figure 8:
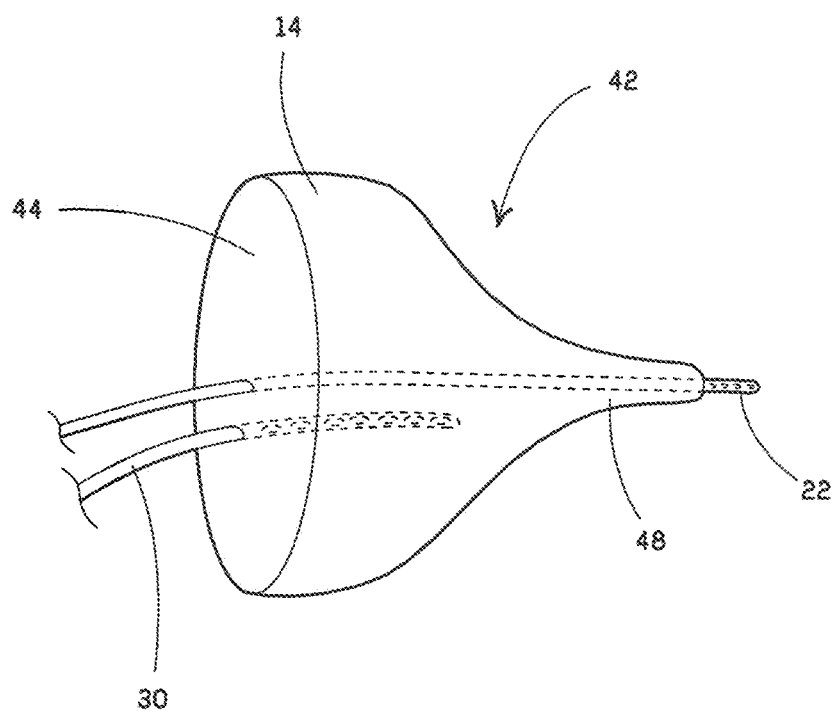
FIG. 8 is a diagrammatic view of another device in accordance with the invention.

A yet further endoVAC device 42 in accordance with the invention is shown in FIG. 8. In this device the sponge 14 is funnel shaped wherein the drainage tube 22 and the suction tube 30 enter the distal face 44 of the sponge, the distal face 44 of the sponge being otherwise sealed against egress of gas and fluid into the sponge as described above. As shown, that portion of the suction tube 30 within the sponge is provided with a number of through openings along its side wall, and the outer diameter of the sponge generally decreases in the distal to proximal direction of the sponge forming a projection of the sponge in the form of a shaft 48 from which the drainage tube 22 extends. The shaft 48 of the sponge can be inserted into a resected end of duct such as the pancreatic duct to assist healing in a pancreatojejunostomy in which the resected pancreas is surgically sutured to the middle region of the small intestine between the duodenum and ileum known as the jejunum. The pancreatic duct carries pancreatic juice from the pancreas to the small intestine. Pancreatic juice is alkaline and contains enzymes which act to break down fat, and so can cause significant damage outside of the intestine. The "leakage rate" for pancreatojejunostomies is in the order of about 15%.

Figure 9:
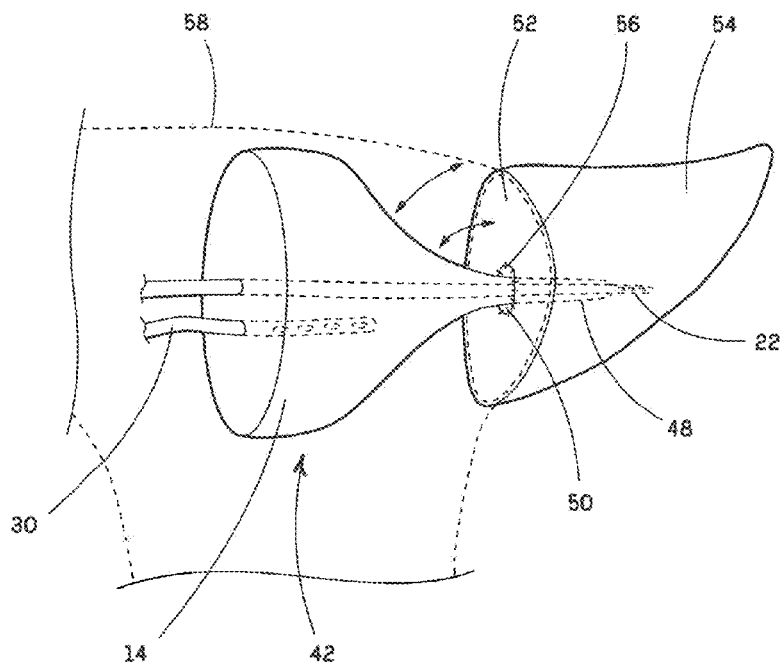
FIG. 9 illustrates the device of FIG. 8 inserted in the pancreatic duct of a pancreas sutured to the jejunum of the small intestine in a pancreatojejunostomy.

An example of a pancreatojejunostomy technique in which the exposed opening of the pancreatic duct 50 in a resected end 52 of the pancreas generally indicated by the numeral 54 is sutured to the mucosa of the jejunum by sutures 56 such that the duct opens into the jejunum 58 through an opening surgically formed in the jejunum is illustrated in FIG. 9. In the embodiment shown, the endoVAC device 42 is located within the lumen of the jejunum and the projecting shaft 48 of the sponge 14 is inserted into the open end of the pancreatic duct 50. The suction applied to the sponge via the suction tube 30 may assist to not only facilitate healing of the resected end of the pancreatic duct but also the suturing injury to the mucosa of the jejunum. The side wall of the jejunum adjacent to the pancreatic duct would also be expected to approximate to the funnel shape of the sponge, the suction applied to the sponge by the suction tube assisting to retain the side wall of the jejunum against the sponge and the shaft 48 of the sponge in position within the pancreatic duct. That is, the outer peripheral face of the sponge and at least the endoluminal surface of the jejunum about the sponge would change shape under the effect of the applied suction to conform to each other as indicated by the double headed arrows.

In some embodiments, at least that portion of the drainage tube 22 within the sponge extending longitudinally through the shaft can comprise an expandable stent sealed from the surrounding through passageway of the sponge by an expandable sleeve or layer of a suitable plastics material. Alternatively, for instance, the through passageway of the sponge in which the stent is received may sealed from the stent in some other manner. As shown in FIG. 8 and FIG. 9, the shaft 48 of the sponge tapers in the distal to proximal direction. However, in other embodiments, the diameter of the sponge's shaft 48 may be essentially constant. Further, the proximal end of the shaft 48 may be sealed against egress of bodily fluids into the sponge although this is not essential in all embodiments of this type as the exposed proximal end of the shaft 48 when in position in the pancreatic or other duct and pressed against the surrounding endoluminal surface of the duct will typically be of minimal thickness.

Figure 10:
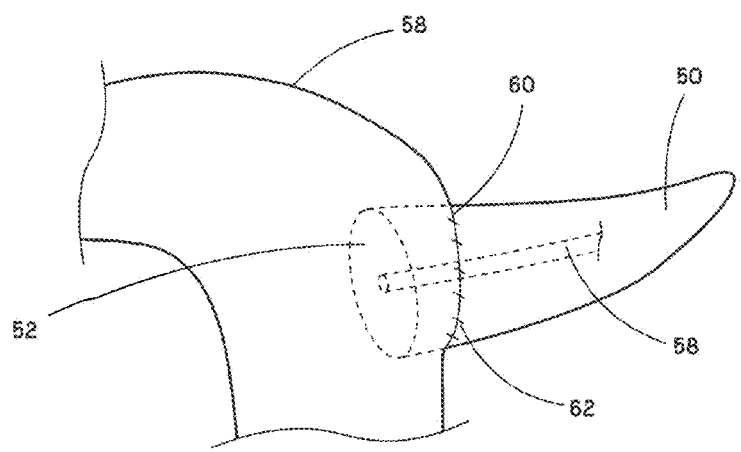
FIG. 10 illustrates a pancreas sutured to the jejumum of the small intestine in a pancreatojejunostomy employing the "dunk technique"

A further pancreatojejunostomy technique in which the entire resected end portion of the pancreas is inserted into an opening 60 formed the side wall of the jejunum 58 whereby the opening in the side wall is sutured to the pancreas by sutures 62 is illustrated in FIG. 10. The shaft 48 of the endoVAC device 42 is again inserted into the resected opening of the pancreatic duct 58 to assist healing of the duct and resected face 52 of the pancreas, as well as the suturing injury to the pancreas and jejunum. As in the embodiment illustrated in FIG. 9, contact of the funnel shaped main body of the sponge 14 with the endoluminal surface of the jejunum and the resected face of the pancreas 54 under the action of the suction applied to the sponge via the suction tube 30 further assists to retain the sponge in position.

The invention will be described further below by way of non-limiting Examples of the use of an endoVAC device embodied by the invention.

EXAMPLE 1

Healing of Rectal Anastomotic Leaks in a Swine Model

Low anterior resection has a leak rate of 8-24%, which carries significant potential morbidity and mortality. A diverting ileostomy is often used for high-risk anastomoses, but its creation and reversal can carry additional morbidity and surgical risk. Thus, an alternative method was sought to manage anastomotic complications after rectal surgery. Negative pressure therapy has been used in superficial wounds but to the knowledge of the inventor, has not previously been used to benefit anastomoses. Of concern is the fecal stream through the anastomosis and to provide for this the inventor developed a negative pressure endoluminal vacuum technology with a diverting proximal sump system. The study described below evaluates the use of such a device in low rectal anastomoses in a swine model.

1.1 Overview

After bowel prep, all pigs underwent rectal resection with primary anastomosis.

A 2 cm defect was then created in the staple line. In the treatment (vac) group, an endoluminal vacuum device having a proximal sump (referred to herein as an "endoVac" device) was inserted and kept to low continuous wall suction for 5 days postoperatively. A second group (Control) had no device placed. During the experiment, all animals were kept NPO and given total parenteral nutrition. After 5 days, pigs were studied using contrast enema and gross necropsy. Specimens were evaluated with H&E histology for mucosal integrity as well as location and density of inflammatory response.

Fourteen pigs were randomly assigned into treatment (10) or control (4) groups. All treatment pigs tolerated 5 days of postoperative recovery after device placement. Of these, 9 had complete closure of the 2 cm defect by day 5 on BE. One had a contained leak. Of the 4 control pigs (no device implanted), 3 leaked (2 contained, 1 uncontained) and one was intact (Chi square for postoperative leak: p=0.041). Three of these pigs were euthanized prior to completion of the experiment due to peritonitis. On histology, the vac treatment group had only minimal mucosal and serosal inflammation, with early granulation tissue seen. The Control group had extensive mucosal damage with associated serositis.

As shown by this study, endoluminal vacuum therapy using an endoVac device in accordance with the invention is well tolerated in the swine model. This therapy was successful in closing anastomotic defects in 90% of cases.

1.2 Objective of the Study

The study utilized a vacuum-assisted closure device placed within the bowel lumen to heal anastomotic leaks in the rectum following a low anterior resection. This endoluminal technique also provided a proximal sump (proximal sump port) to eliminate waste. A randomized, controlled trial in a pig survival model was conducted to test the use of endoluminal vacuum therapy with a proximal sump to increase closure of anastomotic leaks following rectal resection and reduce leak-related morbidity leading to lower rates of intra-abdominal sepsis. The secondary endpoint was to evaluate mucosal integrity and inflammation at the leak site.

1.3 Study Design and Interventions

The study was approved by the Institutional Animal Care and Use Committee (IACUC) of the University of Virginia, Charlottesville, Va., USA. The protocol ensured the appropriate care, use, and humane treatment of the animals being used for research in accordance with the Animal Welfare Act (CFR 9 as amended, USA) and the Guide for the Care and Use of Laboratory Animals, $8^{th}$ edition, 2010, National Research Council, National Academies Press, Washington, D.C., USA).

Pig Characteristics and Operative Preparation

The study used 14 female Yorkshire pigs (60- to 80-lbs). Upon arrival to the vivarium, pigs were kept in standard husbandry conditions, fed a Teklad 7037 miniswine diet, and allowed to acclimate for 72 hours. Food was withheld 48 hours prior to surgery and pigs were provided ad libitum access to drinking water containing 50 g sucrose per liter. Twenty-four hours prior to surgery, pigs were given 24 fluid ounces of magnesium citrate either in their drinking water or via gastric intubation under brief anesthesia.

Anesthesia and Surgical Approach

Figure 11:
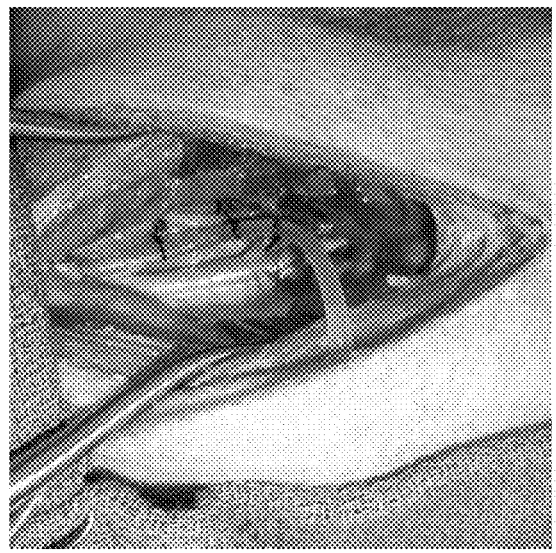
FIGS. 11 and 12 are photographs showing an indwelling silastic catheter implanted in the internal jugular vein of a swine animal model (FIG. 11) to provide for central venous access and which is tunneled subcutaneously to exit near the shoulders of the animal (FIG. 12) to facilitate postoperative restraint.
Figure 12:
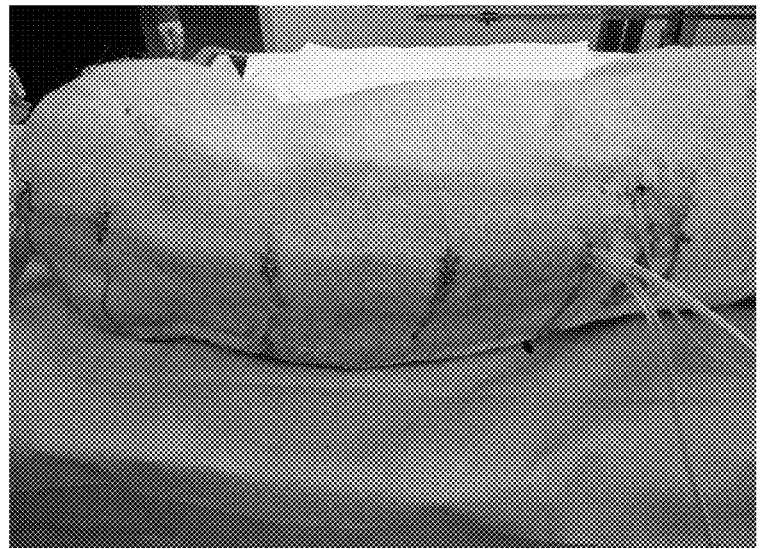
Figure 14:
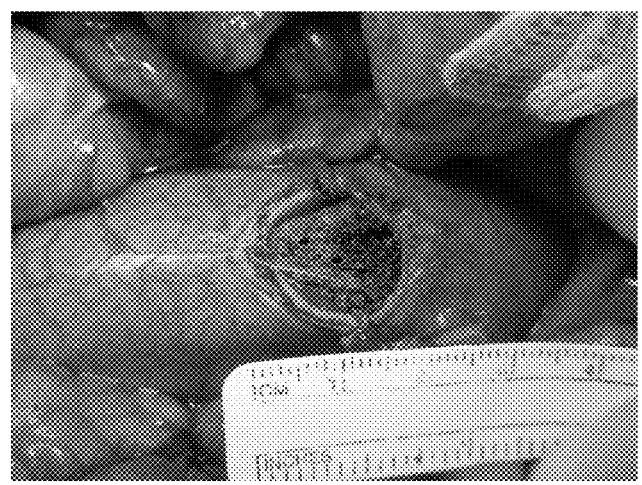
FIG. 14 is a photograph showing the device of FIG. 13 underlying a 2 cm anastomotic defect in the swine model.

On the day of surgery anesthesia was induced with intramuscular (IM) xylazine 2 mg/Kg and telazol 6 mg/kg, once recumbent glycopyrolate 0.01 mg/Kg was administered IM, long-acting tetracycline (LA-200, Pfizer) 9 mg/Kg IM and enrofloxacin (Baytril 100, Bayer) 7.5 mg/Kg IM. The pigs were intubated and maintained on 2.5% isoflurane in oxygen and monitored using standard cardiopulmonary monitoring. Warm lactated Ringer's solution (LRS) was administered intravenously (IV) during surgery at 5 ml/kg/hr and animals were placed on a warm water circulating blanket to prevent hypothermia. The neck, back and abdomen were shaved and the skin prepared for aseptic surgery. A transdermal fentanyl patch (75 µg/hr) was placed on the thoracic skin and 0.3 mg buprenorphine was administered IV once. The pigs were prepped and draped in the usual sterile fashion and an indwelling silastic catheter (0.062" ID×0.125" OD) was implanted in the internal jugular vein (FIG. 11) and tunneled subcutaneously to exit caudal to the ipsilateral scapula (FIG. 12). A midline lower abdominal incision was then made, and the peritoneal cavity entered sharply. The rectosigmoid colon was mobilized and approximately 5 cm of rectum was resected in the standard fashion. The distal colon was primarily re-anastomosed to the rectum using a 21-mm ENDO-PATH™ endoscopic curved intraluminal circular stapler (Ethicon Endo-Surgery, Inc, Cincinnati, Ohio, USA). In all pigs, a 2 cm defect was then made sharply in the staple line, leaving a visible gap in the anastomosis (FIG. 14).

Figure 13:
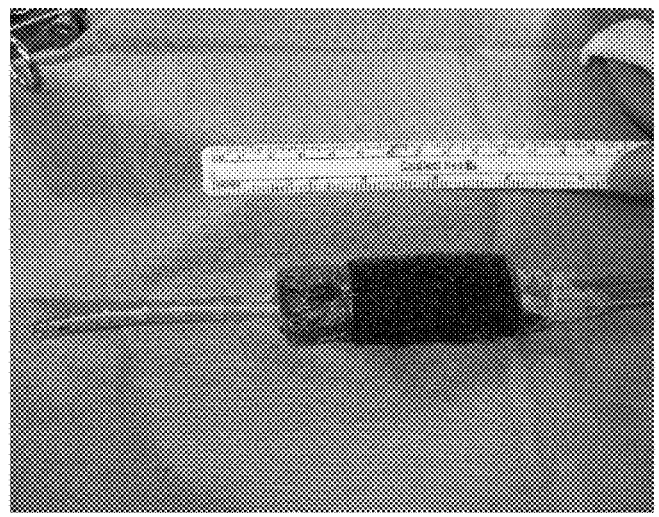
FIG. 13 is a photograph of a further device embodied by the invention with a drainage tube protruding from its proximal end, for use in healing a rectal anastomosis in a study utilising the swine model illustrated in FIG. 11 and FIG. 12.

The pigs were randomly assigned to either the study or control group. The pigs were scheduled to facilitate scheduling of necessary equipment including suction and fluoroscopy equipment, and this decision was made before beginning the operation. Pigs in the study group underwent placement of a dual chamber sump vacuum system in accordance with the present invention. (FIG. 13). This was fashioned using black GranuFoam™ sponge (Kinetic Concepts, Inc., San Antonio, Tex., USA) arranged cylindrically around size 16 French sump tubes (Bard Medical, Covington, Ga., USA) one of the tubes acting as the drainage tube 22 and the other as the suction tube 30. The cylindrical tube of open pore sponge was cut lengthwise and the tubing sutured in position within the sponge to provide the suction tube. Further tubing forming the drainage tube 22 was then placed in the sponge and sutured in position to secure it to the sponge and to the suction tube. The sponge was then sutured longitudinally closed over the drainage and suction tubes 22 and 30, and impervious tape was used to seal the exposed proximal and distal ends of the sponge. The drainage tube 22 protruded from the proximal end of the sponge and had a plurality of spaced apart through openings 26 forward of the sponge, the sponge and the drainage tube defining the diverting proximal sump system of the device. This endoluminal vacuum device was then placed manually into the rectum across the anastomotic site. The proximal sump port terminated in the colon proximal to the anastomosis, and was hooked up to a suction unit at pressures of 75 to 140 mmHg. The distal vacuum port terminated within the GranuFoam sponge and was hooked up to a separate vacuum system with pressures of 5.5 mmHg to 140 mmHg. The vacuum tubing exited into the perirectal tissues, and was tunneled subcutaneously to terminate posterior to the scapula. This was done to facilitate restraint of the animals. The anus was sewn closed with silk suture. In all pigs, the abdomen was closed in a running fashion with #1 PDS and the skin closed with staples.

Postoperative Care

Postoperative continuous total parenteral nutrition (TPN) and LRS was administered via central line. Resting energy requirement (RER) was calculated as 35 Kcal/kg/day, 80% of calories provided by fat (Liposyn II, Hospira) and 20% by glucose (50% Glucose, Butler-Schein). Amino acids were supplemented at 4 gm/100 Kcal/day (10% Amino Acid, Aminosyn-sulfite free) and potassium concentration was adjusted to 30 mEq/L. TPN was given at a rate to delivery RER over 24 hrs and LRS was provided at 1 ml/kg/hr. Serum biochemistry was performed on day 1 and 5 to assess hepatic and renal function as well as adequate hydration. During the period between surgery and euthanasia pig were placed in a harness (Lomir) with conduit to protect IV and vacuum lines, and their motion was partially restrained with a harness that prevented turning but allowed them to stand and move with restriction in an 18 square-feet elevated run. Twice daily, the pigs were tranquilized with 5 mg diazepam and 10 mg acetylpromazine IV to facilitate temperature, pulse, respiration and physical examination by veterinary staff Pigs exhibiting signs of peritonitis, which included tachycardia, peritoneal signs, fever, or discomfort unable to be relieved with fentanyl or buprenorphine were removed from the study and euthanized.

Macroscopic Evaluation

Pigs were weighed preoperatively and after euthanasia. On postoperative day 5 pigs were euthanized with Euthasol (Vibac), the endoluminal vacuum device removed where appropriate, and a postmortem lower GI with contrast (50% Hypaque diluted) was performed and recorded on an OEC 8800 C-arm fluoroscope. At necropsy, exploratory reopening of previous laparotomy was performed and the peritoneal cavity examined for evidence of peritonitis, abscess, anastomotic fistulae, and adhesions.

Histopathology

Rectal anastomotic sites were excised and fixed in formalin. The specimens were dissected, and sections of the enterotomy site, uninvolved rectum, and any atypical appearing areas were taken. The sections were paraffin embedded, cut at 5-micrometer intervals with a standard microtome, and stained with hematoxylin and eosin (H&E). Slides were evaluated by a pathologist for mucosal integrity, overall inflammatory response, presence of serositis, mucosal necrosis, and/or fibrinous adhesions. Inflammatory response was evaluated adjacent to the enterotomy site, and graded as mild, moderate, or severe, with mild representing increased mucosal inflammation, moderate representing increased inflammation with crypt loss, and severe meaning complete absence of crypts. Serositis was scored as mild if minimal serosal inflammation was present, and moderate if inflammation and fibrinous adhesions were seen. Adhesions to any adjacent abdominal organs were recorded. The pathologist was blinded as to which specimens came from control pigs versus the pigs subjected to endoluminal vacuum therapy with the endoVac device embodied by the invention.

Statistical Analysis

This was a feasibility study and its original intent was not to provide statistical significance, but to evaluate feasibility of employing an endoVac device to aid in closing anastomotic defects. This study was not powered a priori. A Fisher's exact test, however, was used to calculate statistical difference in leak between control and vac treatment groups.

1.4 Results

Gross Evaluation and Fluoroscopy

Figure 15:
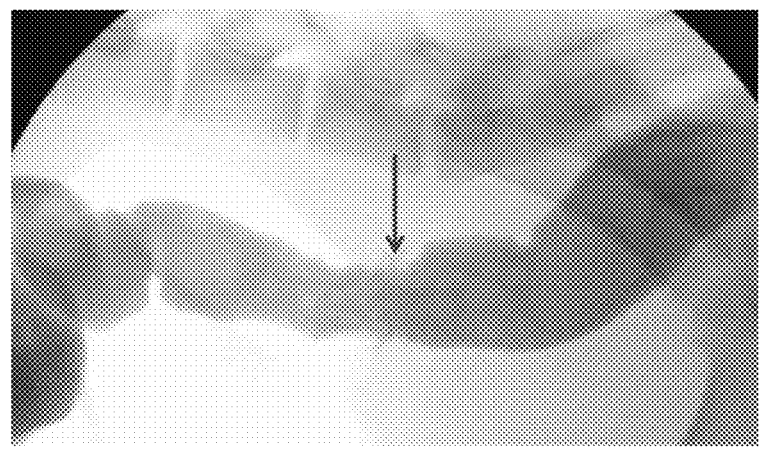
FIG. 15 is a photograph illustrating complete healing of the anastomotic defect in the swine model on fluoroscopic study by day 5 (postoperative)
Figure 16:
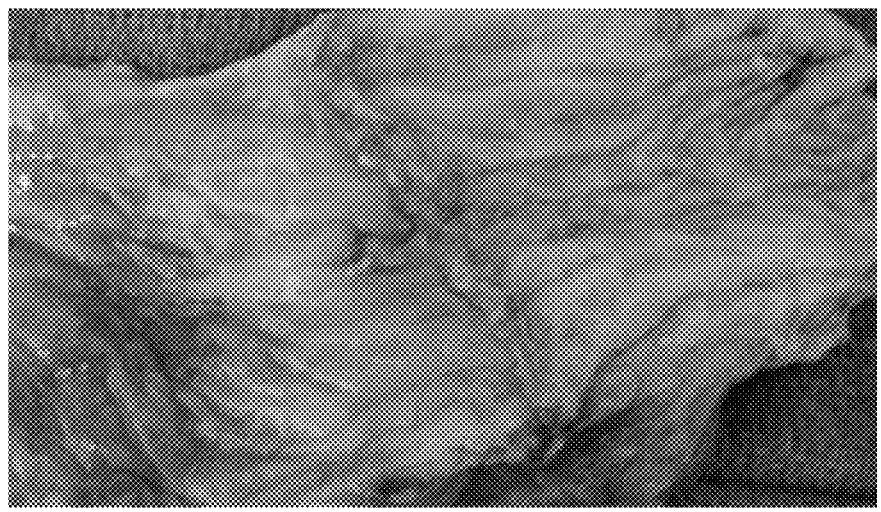
FIG. 16 is a photograph illustrating gross evaluation demonstrating there was no residual defect in the anastomis on day 5 (postoperative).

Ten pigs had an endoVac placed and were part of the experimental treatment group. All 10 tolerated 5 days of therapy. Nine had complete closure on postmortem fluoroscopy (see FIG. 15, the anastomosis is indicated by the arrow). One had a contained leak near the anastomotic site, with a 5 cm abscess on necropsy. No leaks on gross necropsy were seen in the 9 pigs with complete healing (FIG. 16). There was a scar seen at the previous anastomotic site. In two cases, adjacent structures (bladder, fallopian tube) had formed a flap over the anastomotic site to create the seal.

Four pigs comprised the control group and did not undergo vacuum therapy. Three of these had a leak on fluoroscopy (2 contained, one uncontained). All had turbid fluid in the abdomen, and the pigs with contained leaks had abscesses seen adjacent to the anastomosis. Three of these four pigs had to be removed from the study early due to signs of sepsis. Thus, the p value for postoperative leak is 0.0410 in this study.

Weight and Laboratory Results

Control pigs weighed an average of 27 kg at the beginning of the study and 28 kg at the conclusion. Experimental pigs' mean weight was 30 kg at both the beginning and the end of the study. White blood cell (WBC) count in the Control group averaged 10.9 at the beginning, and increased to 19.1 by the end of the study. WBC count in the treatment group averaged 18.8 at the beginning and 26.7 at the end of the study. Of the remaining chemistry studies, there was no significant difference between the groups during the course of the study (see Table 1).

TABLE 1

Study data summary

| Pig # | Control/exp | Pressure | Leak? | Leak type | Fluoroscopy | Necropsy | Sac Day | WBC | Expt start | Expt end |
|---|---|---|---|---|---|---|---|---|---|---|
| 8 | C | n/a | Y | Contained | No leak | 4 cm abscess | 3 | 11/19 | | |
| 13 | C | n/a | Y | Uncontained | | | 5 | | 9/12 | 9/17 |
| 14 | C | n/a | Y | Contained | Leak | | 3 | | | |
| 19 or 18? | C | n/a | N | n/a | stenosis | Turbid free fluid, round lig patch | 2 | 36 | 11/3 | 11/5 |
| 4 | E | 11 | N | | | No defect | 5 | 15/19 | 5/10 | 5/15 |
| 5 (44) | E | 11 | N | | No leak | Bladder, fallopian tube | 5 | | | 7/12 |
| 6 | E | 11 | N | | No leak | mod adhesion | 5 | NR | | 7/18 |
| 7 | E | 11 | N | | | No defect | 5 | 15/NR | 8/11 | 8/16 |
| 9 | NSE | 11 | | | Leak | | 5 | | | |
| 10 | E | 11 | N | | | | 5 | | | |
| 11 | NSE | 11 | | Contained | | | | | | 9/7 |
| 12 | E | 5.5 | Y | Contained | | | 5 | | 9/7 | 9/12 |
| 15 | E | 140 | N | | No leak | Bruising near VAC site, jejunum patch | 5 | | | 10/17 |
| 16 | E | 140 | N | | No leak | Bruising near VAC site | 5 | | | 10/25 |
| 17 | E | 100 | N | | No leak | | 5 | | 10/27 | |
| ? | E | | N | | No leak | Serosal patch | 5 | | | 1/8 |

Note:

C = Control group;

E = Treatment group;

NSE = Non-standard experimental modification from standard protocol (Pig 9 - endoVac device with no proximal sump used; Pig 11 - endoVac sponge sewed together with fewer sutures)

Histology Results

Microscopy results are summarized in Table 2 and Table 3. All enterotomy sites had standard microscopic reparative changes including: increased acute and chronic inflammation, and granulation tissue with early scar formation. Use of the endoVac device was associated with decreased rates of mucosal inflammation and crypt dropout (26% vs 75%), decreased rates of prominent serositis (46% vs 75%), and decreased ischemia/mucosal necrosis adjacent to the enterotomy site (27% vs 100%). Fibrinous adhesions with involvement of surrounding abdominal organs (bladder, ovary, and fallopian tubes) was seen frequently in both the control and experimental groups (64% vs 75%). One control pig (pig 8) that operatively contained a leak, showed significant microscopic damage to the rectum, including extensive necrosis and prominent submucosal hemorrhage, with dissection.

TABLE 2

Histologic characteristics of rectal specimen

| Group | Inflammation | Serositis | Adhesions | Ischemia/Necrosis |
|---|---|---|---|---|
| Control (n = 4) | 25% mild 75% moderate | 25% mild 75% moderate | Bladder, ovary, fibrinous (75%) | 100% |
| Exp. (n = 11) | 18% minimal 64% mild 18% moderate | 27% minimal 27% mild 46% moderate | Bladder, fallopian tube, fibrinous (64%) | 27% |

Note:
Exp = Treatment group

TABLE 3

Histologic characteristics of rectal specimen. Chi-square analysis used for adhesions and ischemia/necrosis.

| | Treatment group (n = 11) | Control group (n = 4) | $X^2$ |
|---|---|---|---|
| Inflammation | | | |
| Minimal | 18 | 0 | |
| Mild | 64 | 25 | |
| Moderate | 18 | 75 | |
| Serositis | | | |
| Minimal | 27 | 0 | |
| Mild | 27 | 25 | |
| Moderate | 46 | 75 | |
| Adhesions | 64 | 75 | NS |
| Ischemia/necrosis (no, %) | 27 | 100 | 0.0256 |

The present study proved that endoluminal wound vacuum therapy using a proximal sump as described above is feasible and safe in an animal model. The study was limited by its small sample size and a larger scale study may be beneficial. The postoperative evaluation period in the study was short, and the long-term performance of these anastomoses is unknown. It cannot be assumed that pigs who had complete healing of their leak by day 5 would not have a recurrent leak at that site shortly after removal of the EndoVac device. A follow up study was therefore conducted to evaluate this model with a longer follow-up survival period following removal of the endoVac device. Briefly, 2 pigs were subjected to rectal resection with primary anastomosis and treated by the application of negative pressure to the resulting wound as described above. The endoVac device was removed on postoperative day 5 and the wounds evaluated by fluoroscopy whilst the pigs were sedated to confirm no anastomotic leaks were present. The pigs were then placed on a normal diet for 2 weeks before being euthanased for gross necropsy study and fluoroscopic evaluation of the woumd site. Again, no anastomotic leakage was found in either pig.

In this study, adhesions were seen between the rectum and adjacent structures. There are published data that link negative pressure therapy and enterocutaneous fistulas. This can be of concern given the morbidity associated with rectovaginal and rectovesicular fistulas. However, the minimal inflammation seen on histology in the present study is reassuring, indicating that this is a potentially inconsequential process. Additionally, there is no difference in the rate of adhesion formation in control and vac treatment groups in this study.

1.5 Discussion

Colorectal cancer remains the third most common cancer in both men and women, and the second leading cause of cancer-related death following lung cancer. Of the estimated 149,000 cases of colorectal cancer in the United States in 2008, 28% were rectal.[1] The American Cancer Society predicted approximately 39,870 new cases of rectal cancer in 2011.[2] Operative therapy remains the mainstay of curative rectal cancer treatment. Commonly, an anterior resection with primary anastomosis is performed with or without temporary proximal diversion. Use of an abdominal perineal resection and a permanent stoma has decreased over time.[3]

Anastomotic disruption is a dreaded complication leading to increased re-operation rates, hospital length of stay, cancer recurrence rate, morbidity, and mortality.[4,5,6,7] Anastomotic leaks may result in abscesses, enterocutaneous fistulae, severe sepsis and peritonitis. While the overall reported rates of colorectal anastomotic leaks range from 2.4% to 12%, the lower rectal anastomoses have a markedly higher rate of anastomotic disruption (8 to 24%).[5,6,8,9,10] Proximal diversion, by loop ileostomy or transverse colostomy, has not been shown to prevent anastomotic leaks and therefore are not common practice apart from high-risk anastomoses.[5,9] Classic management of an anastomotic leak required laparotomy, resection or reinforcement of the anastomosis with proximal diversion or a Hartmann's procedure.[6] A proximal diversion without resection of the leaking anastomosis may be a safe alternative.[9,11]

However, regardless of management technique, an anastomotic leak requires additional operative procedures both in the short-term and again remotely to restore bowel continuity. Each operative procedure acquires additional morbidity and surgical risks. Additionally, there is morbidity associated with ostomies as well, and loop ileostomies carry among the highest stomal morbidity.[12] Therefore, an alternative to operative management of the anastomotic leak in the rectum would be of substantial benefit.

Negative pressure therapy was introduced in 1997 by Morykwas and colleagues as a method to expedite healing by secondary intention.[13] They conducted multiple animal experiments introducing their vacuum-assisted closure device using a foam dressing, adhesive drape, and controlled sub-atmospheric pressure to accelerate wound healing. That technique was found to increase local blood perfusion, accelerated granulation tissue formation, decreased tissue bacterial loads, and increased nutrient blood flow.[13,14] Additionally, vacuum therapy decreases local inflammation.[15]

Vacuum-assisted closure devices have numerous clinical applications and have recently been utilized in pre-sacral and para-anastomotic rectal abscesses. The Endo-SPONGE™ (B. Braun Medical, Melsungen, Germany), is a commercially available device and has been shown to be successful in closing abscess cavities from anastomotic leakage without the need for re-operation.[16-21] That technique used an endoscope to reach the abscess cavity, a plastic introducer tube and pushing probe to deploy the Endo-SPONGE™ into the abscess cavity while retracting the plastic tube.[16] The technique also required exchange of the device every 3 to 4 days and approximately one month to fully resolve the cavity. The Endo-SPONGE™ comprises a plug of open-pore sponge material with a suction tube for application of negative pressure to the sponge and in contrast to the endoVac device embodied by the invention utilised in the present study, the endo-SPONGE™ is not provided with a longitudinal passageway for passage of bodily substances through the sponge of the device.

The above study evaluated the use of an endoVac device to close anastomotic leaks in a prospective fashion. Therapy with this device was well tolerated in pigs, and successfully closed 90% of anastomoses. The leak created was ⅓ to ½ of the bowel lumen, and it healed fully as seen on fluoroscopic and necropsy evaluation. None of the animals undergoing therapy had signs of intra-abdominal sepsis. Animals in the control group did not do as well, as expected given their large untreated enterotomy. Leak rate on fluoroscopy for the vac group was significantly lower as compared to control, even in the present small study.

Anastomotic leak after rectal surgery continues to be a significant cause of morbidity and mortality. Risk factors for anastomotic complications include rectal operations, patients with several co-morbidities, radiation, immuno-suppression, and emergency surgery.[4,10] Anastomotic leaks in cancer are also associated with decreased cancer specific survival as well as local recurrence.[22] A diverting proximal stoma, protective against morbidity after rectal surgery, also adds morbidity, cost, and quality of life issues for the patient.

As shown above, 5 days of endoluminal wound vacuum therapy using an endoVac device in accordance with the present invention assists in closure of anastomotic leaks and provides a way to prevent and manage anastomotic leak complications while avoiding a diverting ostomy.

Previous studies have evaluated use of negative pressure wound therapy in healing anastomotic leaks. Several studies have evaluated the Endo-SPONGE™ system.[20,21] Another study by Mees et al describes an endovacuum assisted closure device that significantly accelerated wound healing after colorectal surgery.[17] However, patients using the devices described in the above studies need to be diverted prior to therapy. In contrast, in the present study, endoluminal therapy with an endoVac device in accordance with the invention (i.e., a vacuum system having a proximal sump), was used avoiding proximal stoma diversion.

EXAMPLE 2

Further Swine Animal Model Study

In another study employing the same animal model described above in Example 1, a low rectal anastomoses in a single pig was treated for 5 days with an endoVAC device that was not provided with a drainage tube 22. That is, the endo-VAC device simply comprised an unsealed sponge without a longitudinal through passageway wherein suction was applied to the sponge by a suction tube 30. However, the sponge became contaminated with faecal matter and suction to the sponge was lost resulting in the anastomosis failing to heal and a consequential uncontained leak from the anastomosis (Pig 9, Table 1).

From the above description of the invention it will be understood that a device embodied by the invention may be used to reduce or prevent leaking from a wound in a method of the invention. The wound may, for example, be an anastomosis resulting from surgery. In at least some embodiments the wound treated in accordance with a method of the invention can be an endoluminal surface of the bowel of a patient.

Whilst various embodiments have been described above, it will be understood that numerous various and modifications can be made without departing from the invention. For example, embodiments may be provided in which the expandable element 34 is a stent (e.g., a wire or other suitable stent) that is in a collapsed state when the device is being located in position within the patient and is operably arranged to be expanded to press the outer sponge 14 into contact with the wound and surrounding endoluminal surface in use. The stent will normally be enclosed in an expandable plastic or other covering sealing the stent from the sponge. Any suitable such stent can be employed. Moreover, the internal diameter of the drainage tube 22 can be greater than that of the particular embodiments shown in the accompanying figures which follow and as such, the relative dimensions and proportions of an endoVAC device embodied by the invention can vary and are not limited to those of the currently exemplified embodiments.

Accordingly, the above described embodiments are merely illustrative and not restrictive.

Literature References

1. Park, J, Guillem, J G. Rectal Cancer. Philadelphia: Elsevier Saunders, 2011.
2. N, H, A M, N, M, K et al. SEER Cancer Statistics Review, 1975-2009. 2011
3. Mekras, A, Michalopoulos, A, Papadopoulos, V N et al. Changes in treatment of rectal cancer: increased use of low anterior resection. Tech Coloproctol 2011; 15 Suppl 1:S51-4.
4. Choi, H K, Law, W L, Ho, J W. Leakage after resection and intraperitoneal anastomosis for colorectal malignancy: analysis of risk factors. Dis Colon Rectum 2006; 49:1719-1725.
5. Matthiessen, P, Hallbook, O, Andersson, M et al. Risk factors for anastomotic leakage after anterior resection of the rectum. Colorectal Dis 2004; 6:462-469.
6. Alves, A, Panis, Y, Pocard, M et al. Management of anastomotic leakage after nondiverted large bowel resection. J Am Coll Surg 1999; 189:554-559.
7. Walker, K G, Bell, S W, Rickard, M J et al. Anastomotic leakage is predictive of diminished survival after potentially curative resection for colorectal cancer. Ann Surg 2004; 240:255-259.
8. Platell, C, Barwood, N, Dorfmann, G et al. The incidence of anastomotic leaks in patients undergoing colorectal surgery. Colorectal Dis 2007; 9:71-79.
9. Hedrick, T L, Sawyer, R G, Foley, E F et al. Anastomotic leak and the loop ileostomy: friend or foe? Dis Colon Rectum 2006; 49:1167-1176.
10. Ragg, J L, Watters, D A, Guest, G D. Preoperative risk stratification for mortality and major morbidity in major colorectal surgery. Dis Colon Rectum 2009; 52:1296-1303.
11. Gastinger, I, Marusch, F, Steinert, R et al. Protective defunctioning stoma in low anterior resection for rectal carcinoma. Br J Surg 2005; 92:1137-1142.
12. Park, J J, Del Pino, A, Orsay, C P et al. Stoma complications: the Cook County Hospital experience. Dis Colon Rectum 1999; 42:1575-1580.
13. Morykwas, M J, Argenta, L C, Shelton-Brown, E I et al. Vacuum-assisted closure: a new method for wound control and treatment: animal studies and basic foundation. Ann Plast Surg 1997; 38:553-562.
14. Urschel, J D, Scott, P G, Williams, H T. The effect of mechanical stress on soft and hard tissue repair; a review. Br J Plast Surg 1988; 41:182-186.
15. Norbury, K, Kieswetter, K. Vacuum-assisted closure therapy attenuates the inflammatory response in a porcine acute wound healing model. Wounds 2007, Apr. 1; 19(4): 97-106.
16. Weidenhagen, R, Gruetzner, K U, Wiecken, T et al. Endoscopic vacuum-assisted closure of anastomotic leakage following anterior resection of the rectum: a new method. Surg Endosc 2008; 22:1818-1825.
17. Mees, S T, Palmes, D, Mennigen, R et al. Endo-vacuum assisted closure treatment for rectal anastomotic insufficiency. Dis Colon Rectum 2008; 51:404-410.
18. Bemelman, W A. Vacuum assisted closure in coloproctology. Tech Coloproctol 2009; 13:261-263.
19. Durai, R, Ng, P C. Perirectal abscess following procedure for prolapsed haemorrhoids successfully managed with a combination of VAC sponge and Redivac systems. Tech Coloproctol 2009; 13:307-309.
20. Van Koperen, P J, Van Berge Henegouwen, M I, Slors, J F et al. Endo-sponge treatment of anastomotic leakage after ileo-anal pouch anastomosis: report of two cases. Colorectal Dis 2008; 10:943-944.
21. Arezzo, A, Miegge, A, Garbarini, A et al. Endoluminal vacuum therapy for anastomotic leaks after rectal surgery. Tech Coloproctol 2010; 14:279-281.
22. Docherty, J G, McGregor, J R, Akyol, A M et al. Ann Surg 1995; 221:176-184.

The invention claimed is:

1. A device for applying a negative pressure to an endoluminal surface in the body of a patient to facilitate healing of a wound in the endoluminal surface, comprising: a flexible porous element with a peripheral outer face for contact with the wound, the outer face being defined between opposite proximal and distal ends of the porous element; a suction tube for being connected to a suction source externally of the patient's body and which is in fluid communication with the porous element to apply a negative pressure to the wound via the outer face of the porous element upon operation of the suction source, the porous element having at least one through passageway extending from its proximal end to its distal end for passage of bodily substances of the patient through the porous element separately from any exudate drawn from the wound into the porous element through its said outer face by the applied negative pressure, at least one of the proximal and distal ends of the porous element being otherwise sealed against egress of the bodily substances into the porous element; and a drainage tube for collection and drainage of the bodily substances from the patient, wherein the drainage tube is received in the through passageway of the porous element.

2. A device according to claim 1 wherein the drainage tube projects from the proximal and distal ends of the porous element, the interior of the drainage tube is defined by a surrounding side wall of the tube and a plurality of through openings are provided in the side wall forward of the proximal end of the porous element.

3. A device according to claim 2 wherein a plurality of further through openings are provided in the side wall of the drainage tube rearwardly of the distal end of the porous element.

4. A device according claim 1 wherein at least the proximal end of the porous element is otherwise sealed against egress of the bodily substances into the porous element.

5. A device according to claim 4 wherein the proximal and distal ends of the porous element are otherwise sealed against egress of the bodily substances into the porous element.

6. A device according to claim 1 wherein the porous element is cylindrical with a single longitudinal said through passage, the through passage being defined centrally within the porous element.

7. A device according to claim 1 wherein the porous element is funnel shaped with a projecting shaft for being inserted into an open end of a duct and a wider portion of greater width than the opening of the duct for location outside of the opening, the duct being defined by the endoluminal surface, and the through passageway of the porous element extending longitudinally through the shaft.

8. A device according to claim 7 wherein the distal end of the porous element is otherwise sealed against egress of the bodily substances into the porous element.

9. A device according to claim 1 further comprising an expandable element arranged for expanding the porous element to press the outer face of the porous element against the wound.

10. A device according to claim 9 wherein the expandable element is an inflatable inner core.

11. A device according to claim 9 wherein the expandable element is fabricated from a resilient material biased to an expanded normal resting state.

12. A device according to claim 11 further comprising a hollow locating tube for locating the porous element in position adjacent the endoluminal surface, the expandable element being received in the locating tube in a compressed state and expandable to its resting state externally of the tube.

13. A device according to claim 1 wherein the porous element is formed from an absorbent material.

14. A device according to claim 13 wherein the porous element is a sponge.

15. A method for facilitating healing of a wound in an endoluminal surface in a body of a patient, comprising: providing a device for applying a negative pressure to the wound, the device having a flexible porous element with a peripheral outer face for contact with the wound, the outer face being defined between opposite proximal and distal ends of the porous element, the porous element having at least one through passageway extending from its proximal end to its distal end for passage of bodily substances of the patient through the porous element separately from any exudate drawn from the wound into the porous element through its said outer face by the applied negative pressure at least one of the proximal and distal ends of the porous element being otherwise sealed against egress of the bodily substances into the porous element, and a drainage tube for collection and drainage of the bodily substances from the patient, the drainage tube being received in the through passageway of the porous element;
  locating the device in position such that the porous element is in contact with the wound;
  applying the negative pressure to the wound through the outer face of the porous element via a suction tube in fluid communication with the porous element; and
  draining the bodily substances from the patient through the drainage tube.

16. A method according to claim 15 wherein both the proximal and distal ends of the porous element are otherwise sealed against egress of the bodily substances into the porous element.

17. A method for treating, or reducing potential for, leakage from an anastomosis in an endoluminal surface in a body of a patient, comprising:

providing a device for applying a negative pressure to the anastomosis, the device having a flexible porous element with a peripheral outer face for contact with the anastomosis, the outer face being defined between opposite proximal and distal ends of the porous element, the porous element having at least one through passageway extending from its proximal end to its distal end for passage of bodily substances of the patient through the porous element separately from any exudate drawn from the wound into the porous element through its said outer face by the applied negative pressure, at least one of the proximal and distal ends of the porous element being otherwise sealed against egress of the bodily substances into the porous element, and a drainage tube for collection and drainage of the bodily substances from the patient, the drainage tube being received in the through passageway of the porous element;

locating the device in position such that the porous element is in contact with the anastomosis;

applying the negative pressure to the anastomosis through the outer face of the porous element via a suction tube in fluid communication with the porous element; and draining the bodily substances from the patient through the drainage tube.

18. A method according to claim 17 wherein both the proximal and distal ends of the porous element are otherwise sealed against egress of the bodily substances into the porous element.

19. A device for applying a negative pressure to an endoluminal surface in the body of a patient to facilitate healing of a wound in the endoluminal surface, comprising:

a sponge with a peripheral outer face for contact with the wound, the outer face being defined between opposite proximal and distal ends of the sponge;

a suction tube for being connected to a suction source externally of the patient's body and which is in fluid communication with the sponge to apply a negative pressure to the wound via the outer face of the sponge upon operation of the suction source, the sponge having at least one through passageway extending from its proximal end to its distal end for passage of bodily substances of the patient through the sponge separately from any exudate drawn from the wound into the sponge through its said outer face by the applied negative pressure, the proximal and distal ends of the sponge being otherwise sealed against egress of the bodily substances into the sponge; and a drainage tube for collection and drainage of the bodily substances from the patient, wherein the drainage tube is received in the through passageway of the sponge.

20. A device according to claim 19 wherein the drainage tube projects from the proximal and distal ends of the sponge, the interior of the drainage tube is defined by a surrounding side wall of the tube and a plurality of through openings are provided in the side wall forward of the proximal end of the sponge.

21. A device according to claim 20 wherein a plurality of further through openings are provided in the side wall of the drainage tube rearwardly of the distal end of the sponge.

22. A device according to claim 19 wherein the sponge is cylindrical with a single longitudinal said through passage, the through passageway being defined centrally within the sponge.

* * * * *